United States Patent [19]

Cid et al.

[11] Patent Number: 5,318,957
[45] Date of Patent: Jun. 7, 1994

[54] METHOD OF STIMULATING ANGIOGENESIS

[75] Inventors: Maria C. Cid, Bethesda; Derrick S. Grant, Beltsville; Hynda K. Kleinman, Bethesda; Gary S. Hoffman, Gaithersburg, all of Md.

[73] Assignee: The United States of America as represented by the Department of Health and Human Services, Washington, D.C.

[21] Appl. No.: 939,142

[22] Filed: Sep. 2, 1992

[51] Int. Cl.$^5$ ............................................. A61K 37/10
[52] U.S. Cl. ...................................... 514/8; 530/395
[58] Field of Search .......................... 514/8; 530/395

[56] References Cited

PUBLICATIONS

Agostoni et al., *Am. Heart J.*, 80, 313–318 (1970).
Castell et al., *FEBS Lett.*, 242, 237–239 (1989).
Chapelle et al., *New Engl. J. Med.*, 307, 457–463 (1982).
Cid et al., *Arthritis Rheum.*, (Suppl.) S117 (1991).
Darlington et al., *J. Cell Biol.*, 103, 787–793 (1986).
Fajardo et al., *Lab. Invest.*, 58, 718–724 (1988).
Fauci et al., *Ann. Intern. Med.*, 89, 660–676 (1978).
Folkman et al., *Science*, 235, 442–447 (1987).
Folkman et al., *Nature*, 339, 58–61 (1989).
Furcht et al., *Lab. Invest.*, 55, 505–509 (1986).
Hansen et al., *Cancer*, 60, 1630–1635 (1987).
Iwasa et al., *Biochem. J. Chem.*, 253, 927–930 (1988).
Kino et al., *J. Biol. Chem.*, 257, 4828–4833 (1982).
Kino et al., *J. Biol. Chem.*, 255, 9618–9620 (1980).
Kinsella et al., *Exp. Cell Res.*, 199, 56–62 (1992).
Kubota et al., *J. Cell Biol.*, 107, 1589–1598 (1988).
Kuhajda et al., *New Engl. J. Med.*, 321, 636–641 (1989).
Kuhajda et al., *Proc. Natl. Acad. Sci. USA*, 86, 1188–1192 (1989).
Liotta et al., *Cell*, 64, 327–336 (1991).
Maeda, *J. Biol. Chem.*, 260, 6698–6709 (1985).
Milland et al., *Am. J. Physiol.*, 259, G340–G347 (1990).
Mueller et al., *Obstet. Gynecol.*, 38, 427–435 (1971).
Oh et al., *Cancer Research*, 47, 5120–5126 (1987).
Oh et al., *J. Natl. Cancer Inst.*, 82, 934–940 (1990).
Oliviero et al., *EMBO J.*, 8, 1145–1151 (1989).
Raugei et al., *Nucleic Acids Research*, 11, 5811–5819 (1983).
Roeckel et al., *Ann. Clin. Lab. Sci.*, 2, 440–443 (1972).
Shurbaji et al., *Lab. Invest.*, 64, 52A (1991).
Snyder et al., *Clin. Chim. Acta*, 34, 449–455 (1971).
Thompson et al., *Clin. Chim. Acta*, 180, 227–284 (1989).
vander Straten et al., *EMBO J.*, 2, 1003–1007 (1983).
Weidner et al., *New Engl. J. Med.*, 324, 1–8 (1991).
Yang et al., *Proc. Natl. Acad. Sci. USA*, 80, 5875–5879 (1983).

Primary Examiner—Michael G. Wityshyn
Assistant Examiner—C. Sayala
Attorney, Agent, or Firm—Leydig, Voit & Mayer, Ltd.

[57] ABSTRACT

A method of stimulating angiogenesis in a mammal by administering to a mammal a haptoglobin in an amount effective to stimulate angiogenesis, and a pharmaceutical composition containing a haptoglobin and a pharmaceutically acceptable carrier.

17 Claims, 7 Drawing Sheets

METHOD OF STIMULATING ANGIOGENESIS

TECHNICAL FIELD OF THE INVENTION

The present invention relates to the stimulation of angiogenesis in mammals or in mammalian tissue in vitro. Specifically, the present invention is directed to inducing or enhancing angiogenesis through the administration of a haptoglobin and to pharmaceutical compositions for effecting the inducement or enhancement of angiogenesis.

BACKGROUND OF THE INVENTION

Angiogenesis is the process by which new blood vessels sprout from existing capillaries. This process plays an important role in such widely divergent biological conditions as embryonic development, tumor growth, wound healing, and chronic inflammatory diseases (Folkman et al., Science, 235, 442-447 (1987)).

Angiogenesis has received a great deal of attention recently because of the potential for manipulation to achieve therapeutic effects. For example, angiogenic processes may aid in the healing of wounds and fractures, the vascularizing of synthetic skin grafts, and the enhancement of collateral circulation where there has been vascular occlusion or stenosis.

Angiogenesis is also important for its detrimental effects in certain biological functions. For example, it is well known that tumor vascularization substantially contributes to the progression of cancer. Angiogenesis also plays an important role in diabetic retinopathy, Kaposi sarcoma, pannus formation in rheumatoid arthritis, and other diseases. The control of the angiogenic process, therefore, may be useful in new treatments for a variety of serious diseases.

Endothelial cells line the walls of blood vessels, and capillaries are comprised almost entirely of endothelial cells. The angiogenic process comprises a cascade of events, including protease secretion by endothelial cells, degradation of the basement membrane, migration through the surrounding matrix, proliferation, alignment, differentiation into tube-like structures, and synthesis of a new basement membrane (Furcht et al., Lab. Invest., 55, 505-509 (1986); Liotta et al., Cell, 64, 327-336 (1991)).

Several angiogenic agents with different properties and mechanisms of action are well known in the art. For example, acidic and basic fibroblast growth factor (FGF), transforming growth factor (TGF) alpha and beta, tumor necrosis factor (TNF), platelet-derived growth factor (PGDF), vascular endothelial cell growth factor (VEGF), and angiogenin are potent and well-characterized angiogenic agents. However, the therapeutic applicability of some of these compounds, especially as systemic agents, is limited by their potent pleiotropic effects on various cell types. There remains a need, therefore, for an angiogenic agent with more general applicability.

SUMMARY OF THE INVENTION

It is an object of the present invention to provide a method of controlling, particularly enhancing, angiogenesis with limited or no adverse effects. It is another object of the present invention to provide a method of treating and preventing diseases and ailments involving angiogenesis such as myocardial and cerebral infarctions, mesenteric or limb ischemia, wounds, and vascular occlusion or stenosis. It is a further object of the present invention to provide a means of analyzing diseases in which angiogenesis is undesired, such as diabetic retinopathy, Kaposi sarcoma, and pannus formation in rheumatoid arthritis.

These and other objects of the present invention, as well as additional inventive features, will be apparent from the description of the present invention herein.

It has been surprisingly discovered that haptoglobins induce and enhance angiogenesis. The present invention involves stimulating angiogenesis both vitro and in vivo in mammalian tissue by administering a haptoglobin to a mammal or to mammalian tissue in an amount sufficient to stimulate angiogenesis. Since haptoglobins are glycoproteins that occur naturally in human plasma, none of the harmful side effects of known angiogenic agents are expected. The present invention also contemplates pharmaceutical compositions comprising a pharmaceutically acceptable carrier in combination with a haptoglobin.

DETAILED DESCRIPTION OF THE PREFERRED EMBODIMENTS

Figure 1:
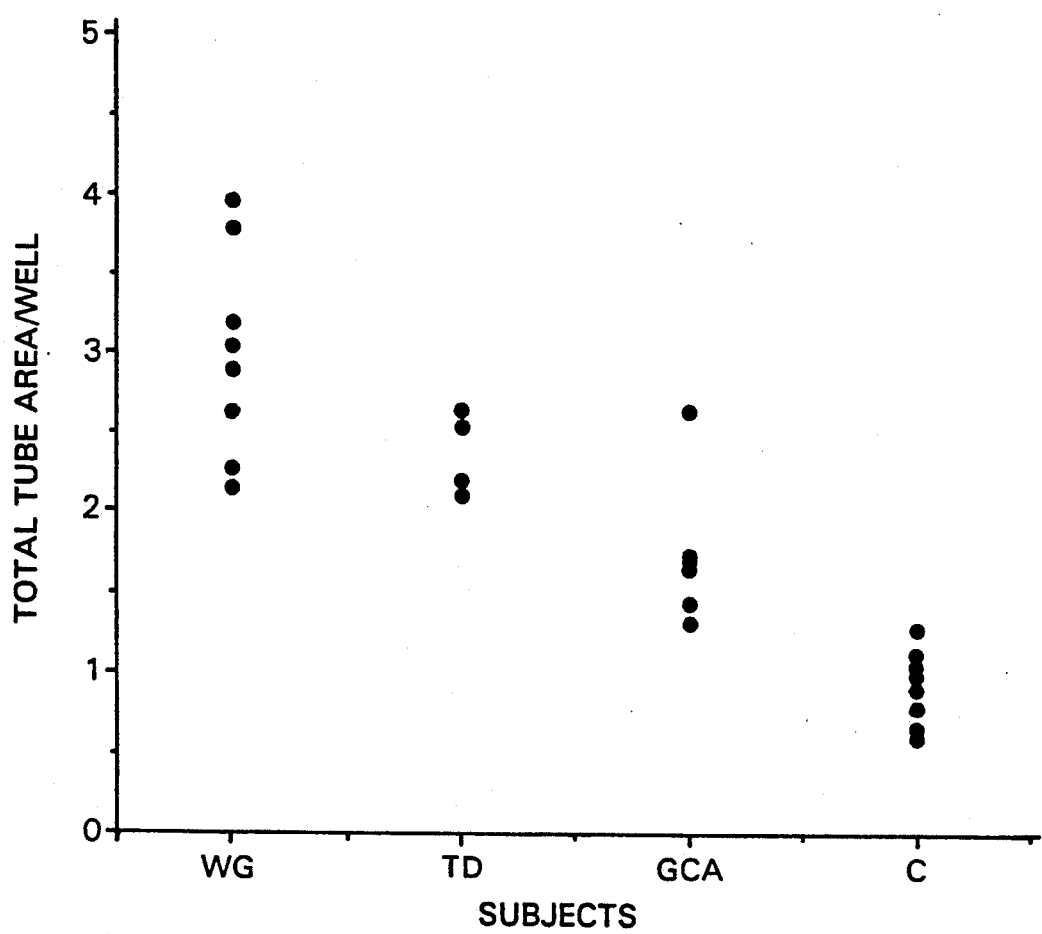
FIG. 1 is plot of total tube area/well ($mm^2$) versus sera obtained from subjects with different vasculitic diseases and illustrates the angiogenic activity of these sera.

The present invention is based on the discovery that haptoglobins stimulate angiogenesis in mammals and in mammalian tissue. It is to be understood by "stimulate angiogenesis" that haptoglobins either enhance or augment a naturally-occurring angiogenic process or, alternately, induce or initiate an angiogenic process. The extent of development of blood vessels resulting from the angiogenic process so stimulated will vary depending on the specific haptoglobin that is used and the concentration of the protein in the regional blood plasma. The present inventive method of stimulating angiogenesis has applicability in both in vitro and in vivo applications.

Haptoglobins are plasma $\alpha_2$-glycoproteins with two polypeptide chains, alpha and beta, linked by disulfide bonds (Roeckel et al., *Ann. Clin. Lab. Sci.*, 2, 440–443 (1972); Raugei et al., *Nucleic Acids Res.*, 11, 5811–5819 (1983)). Haptoglobins are structurally related to serine protease and have high homology in its sequence with urokinase and tissue-type plasminogen activator. Haptoglobins occur naturally in human plasma in significant amounts (1–2 mg/ml), and human haptoglobin is polymorphic, being typically found in one of three major allelic forms: haptoglobin 1.1, haptoglobin 2.2, and the heterozygous haptoglobin 2.1. Differences in the alpha-chain demarcate the different haptoglobin forms.

The haptoglobin gene has been cloned, and the entire genomic DNA sequenced (Yang et al., *Proc. Natl. Acad. Sci. USA*, 80, 5875–5879 (1983); Maeda, *J. Biol. Chem.*, 260, 6698–6709 (1985); vander Straten et al., *EMBO J.*, 2, 1003–1007 (1983)). Haptoglobins are expressed in hepatocytes and in several hepatoma cell lines, where it is induced by several cytokines, particularly IL-6 (Milland et al., *Am. J. Physiol.*, 259, G340–G347 (1990); Iwasa et al., *Biochem. J.*, 253, 927–930 (1988); Darlington et al., *J. Cell Biol.*, 103, 787–793 (1986); Castell et al., *FEBS Lett.*, 242, 237–239 (1989); Oliviero et al., *EMBO J.*, 8, 1145–1151 (1989)). A haptoglobin-related sequence (HPR) is located 2.2 Kb downstream from the haptoglobin gene (Maeda, *J. Biol. Chem.*, 260, 6698–6709 (1985)). It is unclear whether HPR is expressed, and the function of its theoretical product is unknown. Haptoglobin is also present in endothelial cells (Cid et al., *Arthritis Rheum*, 34(suppl), S117 (1991). Previously, haptoglobin's biological function has been perceived as a carrier for free hemoglobin since it is known to form a high-affinity complex with hemoglobin (Kino et al., *J. Biol. Chem.*, 257, 4828–4833 (1982); Kino et al., *J. Biol. Chem.*, 255, 9618–9620 (1980)).

Plasma levels of haptoglobin increase in both acute and chronic inflammatory diseases, and raised serum levels of haptoglobin can also be seen in pregnancy, myocardial infarction, and cancer patients (Hansen et al., *Cancer*, 60, 1630–1635 (1987); Kuhajda et al., *Proc. Natl. Acad. Sci. USA*, 86, 1188–1192 (1989); Agostoni et al., *Am. Heart J.*, 80, 313–318 (1970); Mueller et al., *Obstet. Gynecol.*, 38, 427–435 (1971); Snyder et al., *Clin Chim. Acta*, 34, 449–455 (1971); Oh et al., *Cancer Res.*, 47, 5120–5126 (1987)). In a variety of malignancies, haptoglobin concentration has been shown to correlate with the progression of the disease (Snyder et al., *Clin. Chim. Acta*, 34, 449–455 (1971); Oh et al., *Cancer Res.*, 47, 5120–5126 (1987); Oh et al., *J. Natl. Cancer Inst.*, 82, 934–940 (1990)). The significance of increased levels of haptoglobin in these situations has not been well understood. Heretofore, it has been thought that the increased haptoglobin levels were part of a nonspecific response triggered by systemically-released cytokines that cause altered hepatic synthesis of major plasma proteins (Iwasa et al., *Biochem. J.*, 253, 927–930 (1988); Darlington et al., *J. Cell Biol.*, 103, 787–793 (1986); Castell et al., *FEBS Lett.*, 242, 237–239 (1989)).

Any one of several haptoglobins may be employed in the context of the present invention, including, without limitation, haptoglobin 1.1, haptoglobin 2.1, haptoglobin 2.2, or any of the haptoglobins found in the sera of patients with systemic vasculitis. Systemic vasculitis includes a heterogeneous group of disorders characterized by inflammation of blood vessels. Examples of major systemic vasculitic syndromes are polyarteritis nodosa, Churg-Strauss syndrome, Wegener's granulomatosis (WG), giant-cell (temporal) arteritis (GCA), and Takayasu's disease (TD) (Fauci et al., *Ann. Intern. Med.*, 89, 660–676 (1978)). The inflammatory process often leads to the occlusion or stenosis of the vascular lumen either by thrombus or by myointimal proliferation and fibrosis, with the result being ischemia or infarction.

Other suitable haptoglobins, which may immunochemically and functionally differ from the foregoing haptoglobins, have been described in other pathologic conditions. For example, haptoglobin purified from malignant effusions has immunosuppressive properties that are more potent than that of normal haptoglobin (Oh et al., *J. Natl. Cancer Inst.*, 82, 934–940 (1990); Thompson et al., *Clin. Chim. Acta.*, 180, 227–284 (1989)). Cancer or fetal haptoglobins and normal adult haptoglobin differ primarily as a result of posttranslational modifications that include variations in glycosylation (Oh et al., *J. Natl. Cancer Inst.*, 82, 934–940 (1990); Folkman et al., *Nature*, 339, 58–61 (1989)). Abnormally glycosated haptoglobins may also be associated with chronic inflammatory diseases such as rheumatoid arthritis (Shurbaji et al., *Lab. Invest.*, 64, 52A (1991)). Furthermore, immunohistochemical detection of haptoglobin with antigenic determinants corresponding to the predicted sequence of the HPR product has recently been described in advanced prostatic tumors and in cases of breast cancer (Kuhajda et al., *New Engl. J. Med.*, 321, 636–641 (1989); Kuhajda et al., *Proc. Natl. Acad. Sci. USA*, 86, 1188–1192 (1989); Shurbaji et al., *Lab. Invest.*, 64, 52A (1991)).

The precise mechanism of haptoglobin in stimulating angiogenesis is unknown. Moreover, it is unknown whether haptoglobins influence angiogenesis directly or by interacting with other angiogenic agents such as FGF or TGF beta. It has been observed that both the stimulatory effect of haptoglobin and the inhibitory effect of anti-haptoglobin antibody are effective during the first four hours of the 18–20 hour in vitro tube formation process; thus, it is thought that haptoglobin influences the early steps of the process, such as possibly attachment and migration. Some experiments indicate that haptoglobins strongly stimulate migration of endothelial cells in Boyden chambers. Haptoglobins are present in endothelial cells and are synthesized by endothelial cells. Haptoglobins are released from endothelial cells under gamma interferon stimulation, which suggests that haptoglobins may stimulate angiogenesis in an autocrine manner in an inflammatory environment.

In order to effect angiogenesis, the haptoglobin must act in the presence of certain components of blood plasma which stimulate tube formation or in the presence of substitutes for such components. For example, phorbol esters can substitute for certain unknown plasma components in stimulating tube formation as described in Kinsella et al., *Exp. Cell Res.*, 199, 56–62 (1992).

While the method of the present invention can be practiced in vitro, it has particular usefulness in in vivo applications. The present invention, therefore, includes the administration to an animal, particularly a human, of a therapeutically effective amount of a haptoglobin, as well as pharmaceutical compositions containing a therapeutically effective amount of a haptoglobin and a pharmaceutically acceptable carrier. The use of a haptoglobin in treating animals, particularly humans, to stimulate angiogenesis circumvents the disadvantageous pleiotropic effects of the use of angiogens foreign to the blood plasma.

As regards the in vivo use of the present inventive method, a haptoglobin in the context of the present invention can be administered in any suitable manner, preferably with pharmaceutically acceptable carriers. One skilled in the art will appreciate that suitable methods of administering a haptoglobin in the context of the present invention to an animal are available, and, although more than one route can be used to administer a particular compound, a particular route can provide a more immediate and more effective reaction than another route. Pharmaceutically acceptable carriers are also well-known to those who are skilled in the art. The choice of carrier will be determined in part by the particular haptoglobin, as well as by the particular method used to administer the composition. Accordingly, there is a wide variety of suitable formulations of the pharmaceutical composition of the present invention.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations suitable for topical administration, e.g., directly to a wound, may be similarly prepared through use of appropriate suspending agents, solubilizers, thickening agents, stabilizers, and preservatives. Topical formulations may be also utilized with a means to provide continuous administration of the haptoglobin by, for example, incorporation into slow-release pellets or controlled-release patches. Formulations may be also prepared for direct injection to tissue or organs, e.g., a damaged heart muscle.

The dose of haptoglobin administered to an animal, particularly a human, in the context of the present invention should be sufficient to effect a therapeutic angiogenic response in the animal over a reasonable time frame. The dose will be determined by the strength of the particular haptoglobin employed and the condition of the animal, as well as the body weight of the animal to be treated. For example, the level or affinity or both of its receptor may play a role in regulating haptoglobin's angiogenic activity. The size of the dose also will be determined by the existence, nature, and extent of any adverse side-effects that might accompany the administration of a particular compound. In determining the effective amount of the haptoglobin in the stimulation of angiogenesis, the physician need only evaluate the effects of the haptoglobin in the animal being treated by incrementally increasing the dosage in increments ranging from about 0.1 to about 20 mg/kg body weight to achieve as high a cumulative level of the haptoglobin in the animal as possible without adverse side effects being manifested. The haptoglobin will typically be administered to the animal being treated for a time period ranging from a day to a few weeks, consistent with the clinical condition of the treated animal. This dosage regimen will usually be within the range of about 0.1 to about 500 mg/kg body weight per day, although higher dosage amounts may be required in some situations.

A haptoglobin will be generally administered to a mammal, such as a human, in an amount of about 0.5 mg/kg to about 100 mg/kg of body weight per day. A suitable dose can be administered in suitable subdoses per day, particularly in a prophylactic regimen. The precise treatment level will be dependent upon the response of the animal, e.g., the human patient, being treated. To stimulate angiogenesis in a particular organ, the dose of haptoglobin may be administered by a time-release pellet implanted in that organ. Preferably, the pellet will release the haptoglobin over a period of a few days, e.g., two days. Alternately, a catheterization procedure may be used, whereby the haptoglobin is introduced by means of a catheter.

In the treatment of some individuals with haptoglobins, it may be desirable to utilize a "megadosing" regimen. In such a treatment, a large dose of haptoglobins is administered to an individual, time is allowed for the haptoglobin to act, and then a suitable reagent, e.g., a haptoglobin antibody, is administered to the individual to render the active compound ineffective.

The desirable extent of the angiogenesis will depend on the particular condition or disease being treated, as well as the stability of the patient and possible side-effects. In proper doses and with suitable administration of certain compounds, the present invention provides for a wide range of development of blood vessels, e.g., from little development to essentially full development.

The present invention also provides for a means of controlling or inhibiting angiogenesis by interfering with the role of the haptoglobin in the angiogenic process. This may be accomplished, for example, through use of a haptoglobin antibody. The haptoglobin interfering substance may be administered in the same manner and dosages to mammals, such as humans, as described with respect to the haptoglobin.

The following examples further illustrate the present invention and, of course, should not be construed as in any way limiting its scope.

Example 1

This example illustrates the use of the present invention in stimulating angiogenesis in vitro with the sera from patients with systemic vasculitis as compared to the sera from healthy donors.

Serum samples were obtained from 38 individuals with systemic vasculitis and from 19 healthy donors. Twenty-eight of the vasculitic patients had Wegener's granulomatosis (WG); six had giant-cell arteritis (GCA); and four had Takayasu's disease (TD). Of the WG patients, sixteen had the active disease, five were receiving immunosuppressive therapy and were asymptomatic, and nine were untreated patients in remission. All of the GCA and TD patients had evidence of active disease.

Human umbilical vein endothelial cells (HUVEC) were isolated from fresh placental cords as described in Jaffe et al., *J. Clin. Invest.*, 52, 2745-2756 (1973). The umbilical vein lumen was washed with Hank's balanced salt solution lacking calcium and magnesium (HBSS-) (Gibco Laboratories, Grand Island, N.Y.) and filled with 0.1% collagenase (Boehringer-Mannheim, Indianapolis, Ind.) in Dulbecco's phosphate buffered saline without calcium and magnesium (DPBS-). After a 15-minute incubation at 37° C., the solution and an additional 20 ml HBSS- wash were collected. After washing once in HBSS-, the cells were plated in 100 cm² flasks (Nunc, Naperville, Ill.) and grown until confluence at 37° C. in 5% $CO_2$. The growth medium comprised Medium 199 (Gibco Laboratories, Grand Island, N.Y.) supplemented with 20% bovine calf serum (BCS) (Hyclone laboratories Inc., Logan, Utah), 200 μg/ml serum endothelial cell growth supplement (ECGS) (Collaborative Research Inc., Bedford, Mass.), 100 U/ml penillin-streptomycin, 50 μg/ml gentamicin, 2 mM glutamine (Gibco Laboratories, Grand Island, N.Y.), and 5 U/ml sodium heparin (Fisher Scientific, Fair Lawn N.J.). Cells used for experimentation were from passage 4 to 8.

Matrigel was extracted from the murine Engelbreth-Holm-Swarm tumor as described in Kleinman et al., *Biochemistry*, 25, 312-318 (1986), sterilized with chloroform, and dialyzed against Medium 199. Matrigel is a basement membrane extract. It is polymerizable into a rigid stable gel upon heating at 24°-37° C. A more complete discussion of Matrigel can be found in U.S. Pat. No. 4,829,000.

Twenty-four well plates (Costar, Cambridge, Mass.) were coated with 300 μl of Matrigel which was allowed to polymerize at 37° C. for 30 minutes. HUVEC (30,000/well) suspended in Medium 199 were plated on Matrigel. To this was added sera from either the vasculitic patients or the controls at a concentration of 5% in a final volume of 1 ml. After an overnight incubation at 37° C. in 5% $CO_2$, the capillary-like structures (tubes) were fixed and stained with Diff-Quik (Baxter Healthcare Corp., McGaw Park, Ill.), and the total tube area/well in duplicate wells was measured at 10x magnification with a computerized digitizer (Optomax).

At this low cell density and low serum concentration (5%), conditions are suboptimal for endothelial cell differentiation. Formation of capillary tubes using HUVEC and control serum was marginal, with many incomplete tubes formed. In distinct contrast, the sera from patients with systemic vasculitis readily stimulated tube formation, with sera from patients with WG yielding the best results, followed by sera from patients with TD and from patients with GCA. The results obtained from this evaluation are set forth in FIG. 1, wherein the total tube area/well (mm²) is plotted for each of the different sources of sera. The assay was repeated three times with comparable results.

Example 2

This example illustrates that the sera from WG patients in a more advanced diseased state has a greater angiogenic activity than the sera from other WG patients and healthy controls.

Sera was obtained from 10 patients with active WG, 4 WG patients receiving therapy, 4 untreated WG patients in remission, and 6 healthy controls. The angiogenic activity of the various sera was determined as in Example 1.

Figure 2:
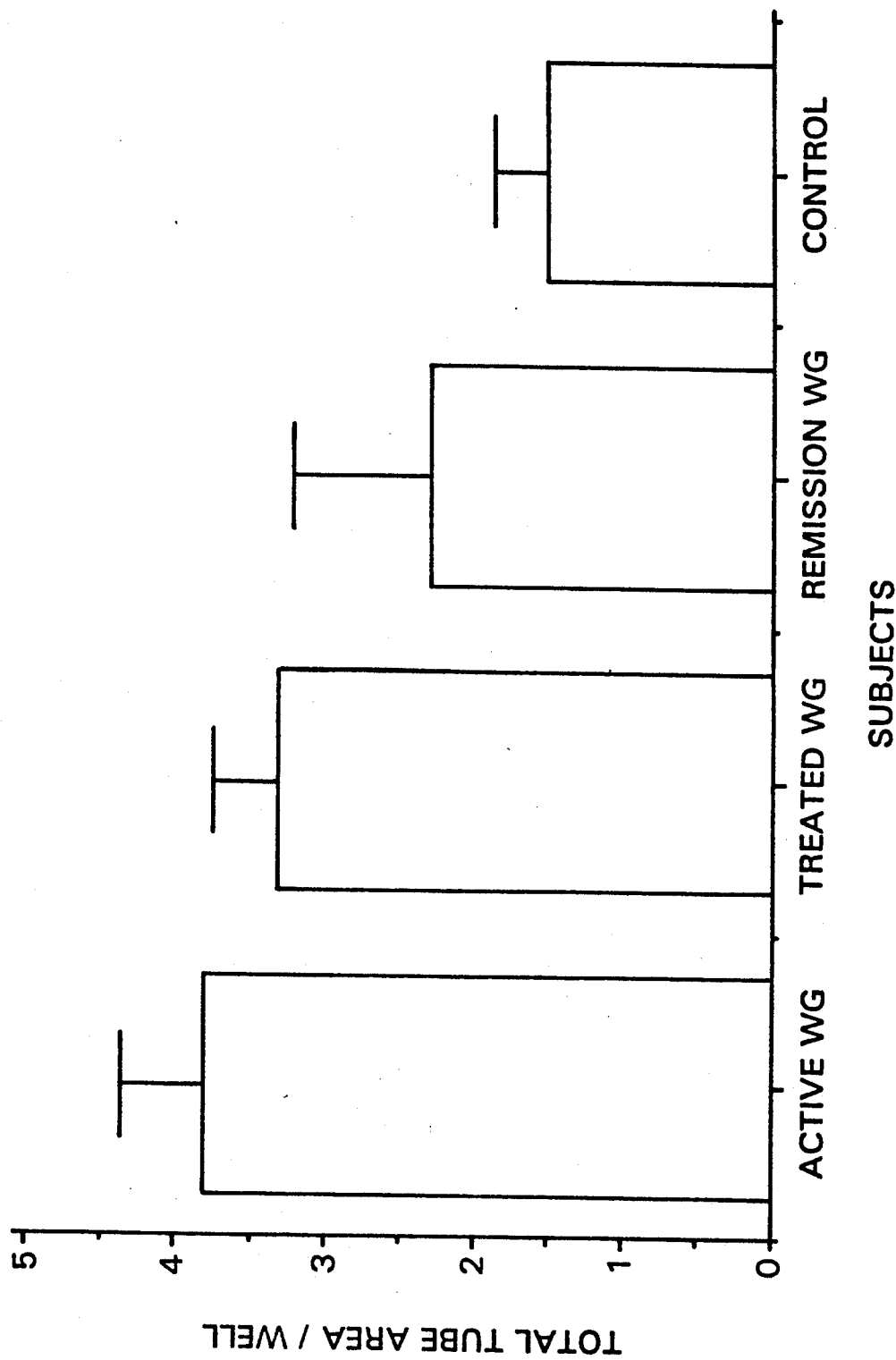
FIG. 2 is a plot of total tube area/well ($mm^2$) versus sera obtained from patients with Wegener's granulomatosis at various disease stages and from controls and illustrates the angiogenic activity of these sera.

A comparison of the effects of the sera from the patients with WG revealed that the sera from the active WG patients stimulated tube formation to a greater extent than sera from those WG patients who were being treated or were in remission, although such sera was still more effective than the control. The results obtained from this evaluation are set forth in FIG. 2, wherein the total tube area/well (mm²) is plotted for each of the different sources of sera.

EXAMPLE 3

This example sets forth the manner in which the angiogenic agents present in WG serum were characterized and confirms that haptoglobins have angiogenic activity.

Sera were obtained from nine patients with WG and 3 healthy controls. Samples of medium containing 14% serum were precipitated with 40% ammonium sulfate, and the serum supernate tested for angiogenic activity in a manner similar to that set forth in Example 1, with the supernate being dialyzed against Medium 199 and tested at a 1:2 dilution.

The supernate derived from the sera of the nine WG patients yielded tube formation results indistinguishable from those obtained with whole serum. These results, however, were abolished upon heating of the supernate. By contrast, no angiogenic activity was found with the precipitate pellet derived from the sera of the nine WG patients, or either the supernate or precipitate pellet derived from the sera of the three healthy controls, when tested for angiogenic activity in the same manner.

Six 1 ml samples of the supernate derived from the sera of the WG patients were chromatographed on Superose 6 by FPLC (Pharmacia LKB Biotechnology Inc., Piscataway, N.J.) using DPBS- as the elutant, and the fractions tested for angiogenic activity as described in Example 1 in the presence of 2% BCS. The fractions with the highest activity were dialyzed against distilled $H_2O$, lyophilized, and electrophoresed in SDS-PAGE as described in Laemmli, *Nature*, 227, 680-685 (1988).

SDS-PAGE of the active FPLC fractions of WG sera under reducing conditions yielded two bands of 45 Kd and 16 Kd, respectively. These same bands were detected at greatly reduced levels in similar fractions from the three samples of the control sera treated in the same manner. The electrophoresed bands were transferred onto a nylon sheet (IMMOBILON) (Millipore Corporation, Bedford, Mass.), fixed with 100% methanol, and stained with freshly prepared Coomassie brilliant blue G solution (Sigma Chemical Co., St. Louis, Mo.). The 45 Kd band was amino-terminal sequenced directly from IMMOBILON paper after transfer from the SDS gel. The sequence of the 18 terminal amino acids of the 45 Kd band was found to be identical to the beta chain of human haptoglobins.

Figure 3:
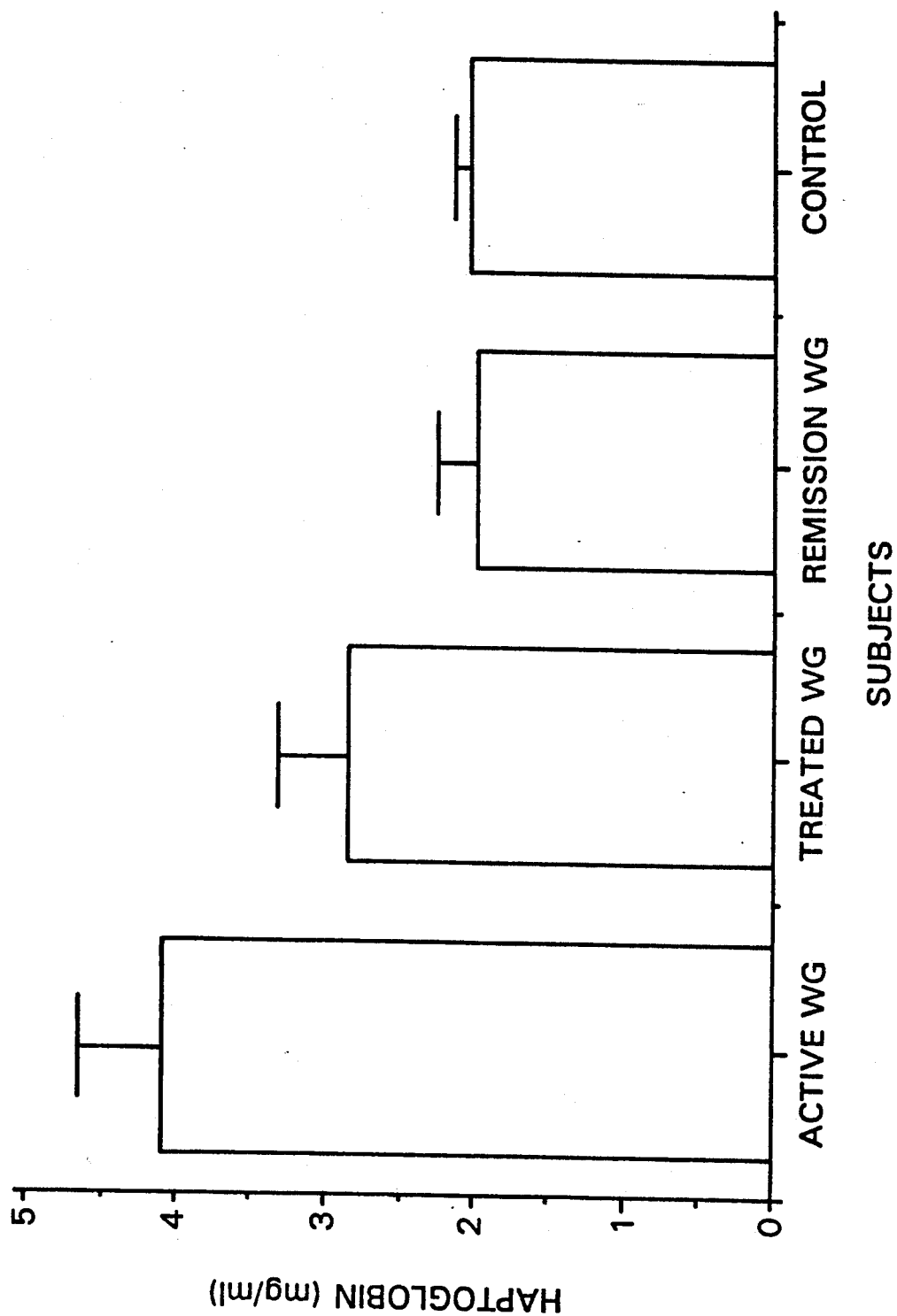
FIG. 3 is a plot of haptoglobin concentration (mg/ml) of the sera obtained from patients with Wegener's granulomatosis at various disease stages and from controls and illustrates the increased haptoglobin concentration in those subjects with active Wegener's granulomatosis.

Haptoglobin concentration was subsequently determined in sera from both WG and normal patients. Haptoglobin serum concentration was measured by nephelometry (American Medical Laboratories Inc., Fairfax, Va.) in 25 patients with WG and 10 healthy controls. Of the 25 patients with WG, ten of the WG patients exhibited the active disease, six of the WG patients were asymptomatic and receiving immunosuppressive therapy, and nine of the WG patients were untreated and in remission. It was found that levels of haptoglobin were elevated during active disease in WG patients, decreased during treatment and improvement, and were similar to controls during untreated remission. The results are depicted in FIG. 3, wherein the determined haptoglobin concentration (mg/ml) is plotted against the WG disease state.

Figure 4:
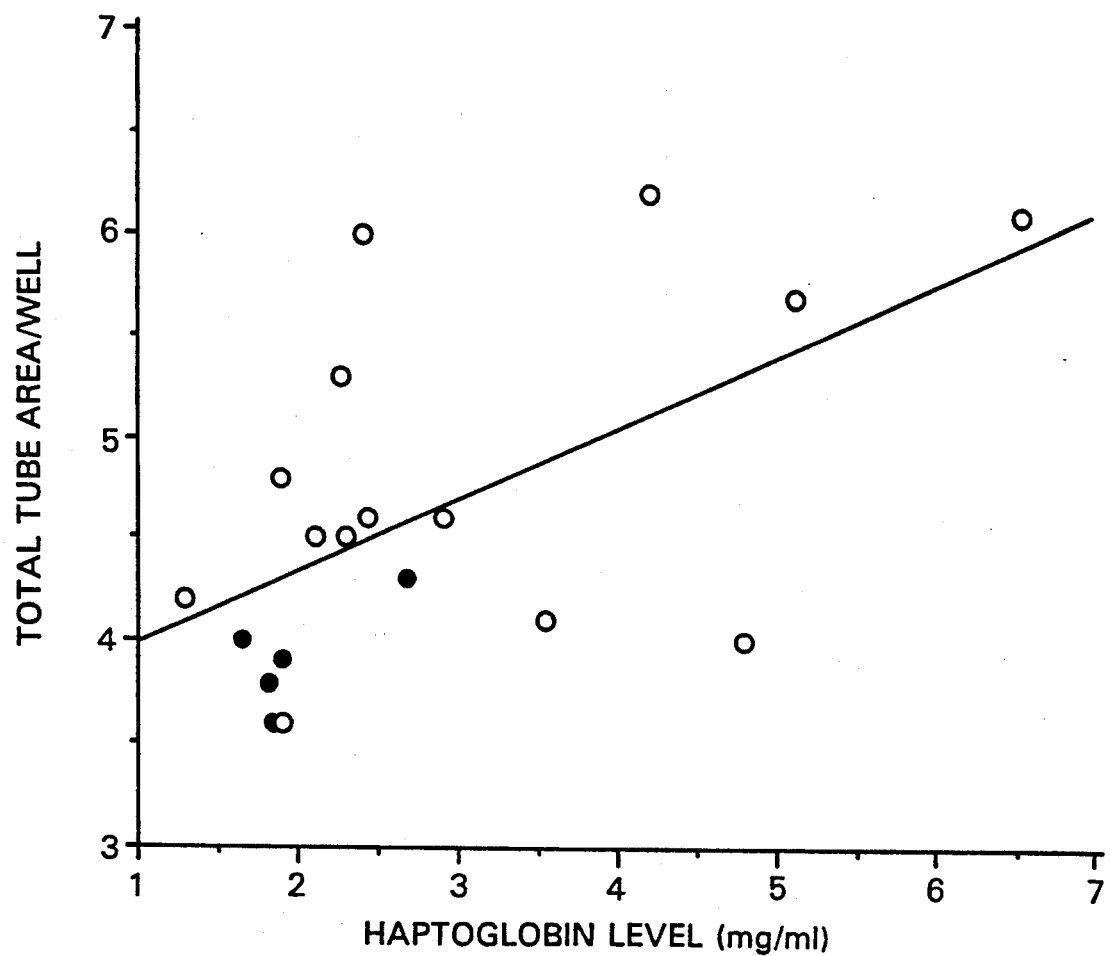
FIG. 4 is a plot of total tube area/well ($mm^2$) versus various haptoglobin amounts (mg/ml) and illustrates the angiogenic activity of haptoglobin from both control (closed circle) and vasculitis (open circle) patients.

The angiogenic activity for the sera of 14 patients with WG and 5 controls were compared with the determined haptoglobin levels in the sera. Angiogenic activity and the haptoglobin levels were determined as described above. Of the 14 patients with WG, six of the WG patients exhibited an active disease state, three of the WG patients were being treated, and five of the WG patients were in remission. The resulting data is depicted in FIG. 4, wherein angiogenic activity measured in total tube area (mm$^2$) is plotted against haptoglobin level (mg/ml) in sera. The comparison reveals the correlation between angiogenic activity and haptoglobin concentration, thus further confirming the angiogenic effect of haptoglobins.

EXAMPLE 4

This example demonstrates the stimulation of angiogenesis in vitro through use of the present invention with purified haptoglobins and further confirms the angiogenic activity of haptoglobins.

Commercially-available haptoglobin purified from pooled human plasma (phenotypes 1.1, 2.1, and 2.2, Sigma Chemical Co., St. Louis, Mo.) at concentrations ranging from 0 to 0.10 mg/ml in 2% bovine calf serum were tested in triplicate in the same in vitro system described in Example 1. Furthermore, the purified IgG fraction of either a rabbit anti-human haptoglobin antiserum (Sigma Chemical Co., St. Louis, Mo.) or non-immune rabbit serum (Zymed, San Francisco, Calif.) was added to the culture medium at a 1:20 dilution and tube formation was assessed as in Example 1.

Figure 5:
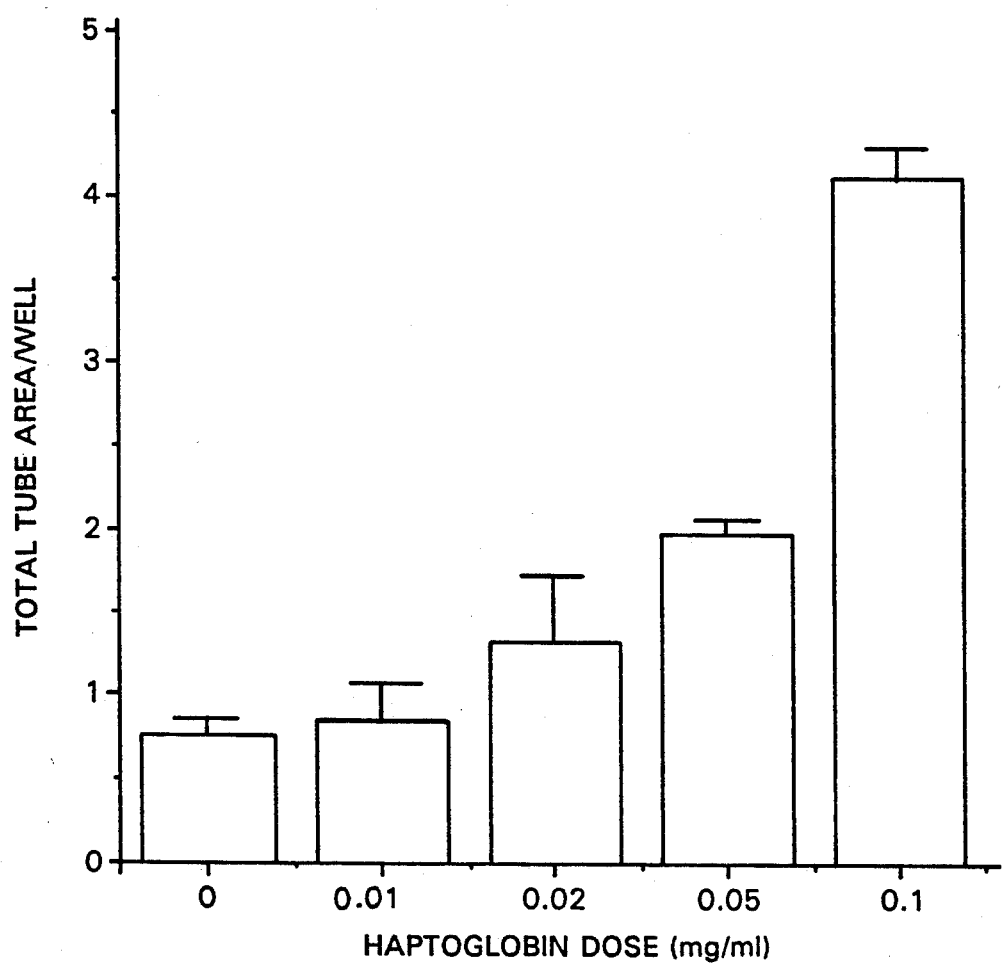
FIG. 5 is a plot of total tube area/well ($mm^2$) versus various haptoglobin amounts (mg/ml) and illustrates that the angiogenic activity of haptoglobin is dose-dependent in vitro.

The results of this analysis are set forth in FIG. 5, wherein total tube area/well (mm$^2$) is plotted against haptoglobin dose (mg/ml). As shown in FIG. 5, tube formation was stimulated in a dose-dependent manner, although the haptoglobins required the presence of serum in order to stimulate in vitro tube formation. A comparison of the relative activities of the various haptoglobin phenotypes revealed that haptoglobin 2.2 was more active than haptoglobin 1.1, and the heterozygous 2.1 form displayed an intermediate activity.

The angiogenic activity of 7% WG serum was partially inhibited by the IgG fraction of a rabbit anti-human-haptoglobin antiserum. Tubes remained well-constituted, and the inhibitory effect primarily involved a decrease in the branching points and the number of interconnected tubes. A similar inhibitory effect of the anti-haptoglobin antibody was observed on the tube-forming activity promoted by complete medium containing 20% bovine calf serum, as well as with respect to the lesser activity present in 7% normal human control sera. The addition of non-immune rabbit IgG did not influence tube formation. These results further demonstrate that haptoglobins have angiogenic activity.

EXAMPLE 5

This example demonstrates the stimulation of angiogenesis in vivo through use of the present invention and purified haptoglobins.

Matrigel liquid at 4° C. was mixed with various concentrations of commercially-obtained haptoglobin 1.1 and 2.1 (Sigma Chemical Co., St. Louis, Mo.) at a final concentration of 0.5, and 2 mg/ml. In some experiments, the haptoglobin was first heat inactivated at 100° C. for 15 minutes. Matrigel alone and with test haptoglobin was injected subcutaneously into athymic mice (NIH beige nude XID) in duplicate. After 10 days, the animals were sacrificed and the Matrigel plugs were removed, fixed in 3.7% formaldehyde, and paraffin embedded. Histological sections were stained with Masson's trichrome. The vessel area in histological sections of the Matrigel plug was measured using a computerized digitalizer (Optomax). A total of 20 fields at 100x magnification were evaluated for each specimen. The experiment was repeated three times.

Figure 6:
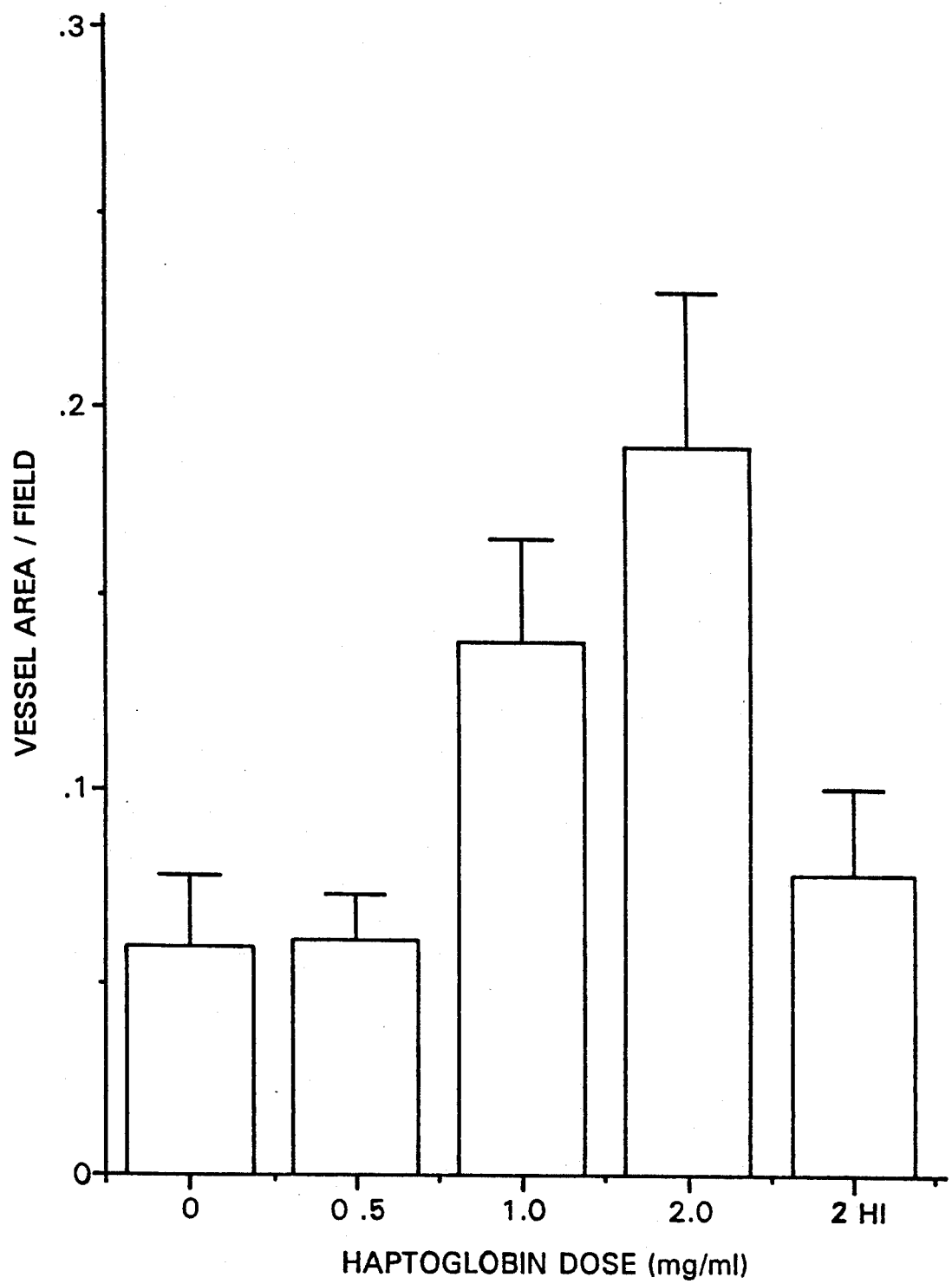
FIG. 6 is a plot of vessel area-field ($mm^2$) versus various haptoglobin amounts (mg/ml) and illustrates that the angiogenic activity of haptoglobin in vivo is dose dependent and that heat-inactivated haptoglobin (HI) is not active.

The results obtained through this experiment are set forth in FIG. 6, wherein vessel area/field (mm$^2$) is plotted against haptoglobin dose (mg/ml). In plugs containing Matrigel alone (i.e., 0 mg/ml haptoglobin), endothelial cells invaded sparsely, mainly from the subcutaneous edge. In distinct contrast, haptoglobin-containing plugs (particularly at 1.0 and 2.0 mg/ml haptoglobin) differed not only in the density but also in the depth that endothelial cells invaded the matrix. Well-constituted and functional vessels were observed. Cell development was dose-specific, and haptoglobin 2.2 at 2 mg/ml, a concentration high in the physiological range, was much more active than haptoglobin 1.1 as studied in vitro. Heat inactivation (HI) strongly reduced the angiogenic activity of the haptoglobins even at a high concentration of haptoglobin (e.g., 2.0 mg/ml haptoglobin).

EXAMPLE 6

This example also illustrates the stimulation of angiogenesis in vivo through use of the present invention.

Although the stimulatory effects of adding haptoglobin to the Matrigel plug are apparent from the results of Example 5, an experiment was formulated in which the effects of any angiogenic agents inherent in Matrigel were eliminated. A disc angiogenesis study was performed, using the procedure described in Fajardo et al., *Lab. Invest.*, 58, 718–24 (1988). The central core (1.5 mm in diameter) of the polyvinyl alcohol foam disc (11 mm in diameter and 1 mm thickness) (Kanebo PVA) was punched and impregnated with phosphate buffered saline (PBS) and haptoglobin at different concentrations. To maintain a slow release, the core was coated with ethylene-vinyl acetate copolymer (Elvax, DuPont, Wilmington, Del.) and replaced in the center of the disc. The flat surfaces were sealed with 0.45 μm Millipore filters (Millipore Corp., Bedford, Mass.) to allow the vessels to penetrate only through the edges. The discs were subsequently implanted subcutaneously into mice through an incision in the abdomen and placed contralaterally by blunt dissection. The discs were removed after 14 days, fixed with 3.7% formaldehyde and embedded in paraffin. Tangential sections were stained with hematoxylin and eosin, and the area penetrated by endothelial cells was measured using the image analyzing system described by Auerbach et al., *Issues Biomed.*, 14, 180–89 (1991).

Figure 7:
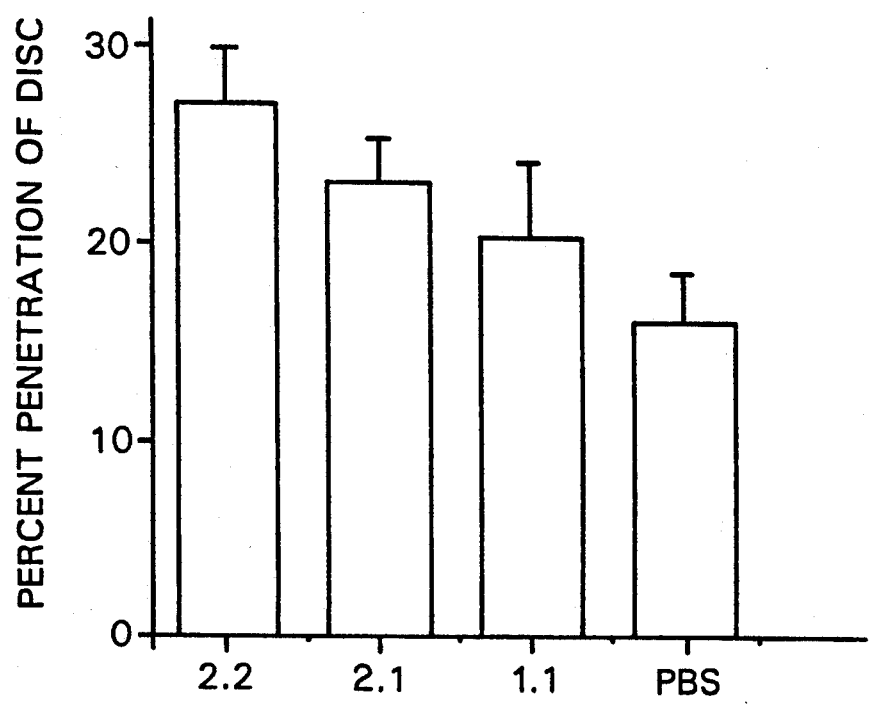
FIG. 7 is a plot of percent vascular penetration of subcutaneously implanted discs containing different haptoglobin types and a PBS control and illustrates the angiogenic activity in vivo of haptoglobin, as well as the differing angiogenic activities of various haptoglobin phenotypes.

The results obtained from this evaluation are set forth in FIG. 7, wherein the percent penetration of the disc is plotted for each of the different samples (i.e., PBS alone and haptoglobins 1.1, 2.1, and 2.2). As is apparent from the results, the best disc penetration was observed with haptoglobin 2.2, followed by haptoglobin 2.1 and then haptoglobin 1.1. All of the haptoglobins exhibited higher disc penetration characteristics than PBS. The level of disc penetration observed with haptoglobin 2.2 (40 μg/disc) is comparable to that observed with 2–4 ng/ml FGF.

All of the references cited herein are hereby incorporated in their entireties by reference.

While this invention has been described with an emphasis on preferred embodiments, it will be obvious to those of ordinary skill in the art that variations in the preferred method and pharmaceutical composition may be used and that it is intended that the invention may be practiced otherwise than as specifically described herein. Accordingly, this invention includes all modifications encompassed within the spirit and scope of the invention as defined by the following claims.

What is claimed is:

1. A method of stimulating angiogenesis in a mammal, which method comprises administering to a mammal a haptoglobin in an amount effective to stimulate angiogenesis.

2. The method of claim 1, wherein said haptoglobin is selected from the group consisting of haptoglobin 1.1, haptoglobin 2.1, haptoglobin 2.2, the haptoglobins found in the sera of patients with systemic vasculitis, and mixtures thereof.

3. The method of claim 2, wherein said haptoglobin is haptoglobin 2.2.

4. The method of claim 2, wherein said haptoglobin is haptoglobin 2.1.

5. The method of claim 2, wherein said haptoglobin is haptoglobin 1.1.

6. The method of claim 2, wherein said haptoglobin is one or a mixture of two or more of the haptoglobins found in the sera of patients with systemic vasculitis.

7. The method of claim 2, wherein said mammal is a human.

8. The method of claim 7, wherein said haptoglobin is administered in an amount sufficient to result in a haptoglobin concentration of at least about 2 mg/ml blood plasma.

9. A method of stimulating angiogenesis in mammalian tissue in vitro, which method comprises contacting mammalian tissue in vitro with a haptoglobin in an amount effective to stimulate angiogenesis.

10. The method of claim 9, wherein said haptoglobin is selected from the group consisting of haptoglobin 1.1, haptoglobin 2.1, haptoglobin 2.2, the haptoglobins found in the sera of patients with systemic vasculitis, and mixtures thereof.

11. The method of claim 10, wherein said haptoglobin is haptoglobin 2.2.

12. The method of claim 10, wherein said haptoglobin is haptoglobin 2.1.

13. The method of claim 10, wherein said haptoglobin is haptoglobin 1.1.

14. The method of claim 10, wherein said haptoglobin is one or a mixture of two or more of the haptoglobins found in the sera of patients with systemic vasculitis.

15. The method of claim 10, wherein said mammalian tissue is human tissue.

16. A pharmaceutical composition comprising a pharmaceutically acceptable carrier and a haptoglobin in a therapeutically effective amount to stimulate angiogenesis.

17. The pharmaceutical composition of claim 16, wherein said haptoglobin is selected from the group consisting of haptoglobin 1.1, haptoglobin 2.1, haptoglobin 2.2, the haptoglobins found in the sera of patients with systemic vasculitis, and mixtures thereof.

* * * * *